United States Patent [19]
Armstrong

[11] Patent Number: 5,411,536
[45] Date of Patent: May 2, 1995

[54] METHOD AND APPARATUS FOR COMMUNICATING DATA BETWEEN MEDICAL DEVICES TO IMPROVE DETECTABILITY OF ERRORS

[75] Inventor: Randolph K. Armstrong, Missouri City, Tex.

[73] Assignee: Intermedics, Inc., Angleton, Tex.

[21] Appl. No.: 71,519

[22] Filed: Jun. 3, 1993

[51] Int. Cl.⁶ .............................................. A61N 1/372
[52] U.S. Cl. ........................................ 607/32; 607/60; 340/870.01; 375/239
[58] Field of Search ..................... 602/32, 60; 128/903; 340/870.01, 870.1, 870.19, 870.22, 870.24; 375/23, 25, 26

[56] References Cited

U.S. PATENT DOCUMENTS

| | | | |
|---|---|---|---|
| 4,569,050 | 2/1986 | Ohme | 371/37 |
| 4,723,244 | 2/1988 | Iacoponi | 371/37 |
| 4,764,769 | 8/1988 | Hayworth et al. | 342/50 |
| 5,179,561 | 1/1993 | Izawa et al. | 371/52 |

FOREIGN PATENT DOCUMENTS

| | | |
|---|---|---|
| 0072611 | 2/1983 | European Pat. Off. . |
| 0107483 | 5/1984 | European Pat. Off. . |
| 0177360 | 4/1986 | European Pat. Off. . |
| 0412427 | 2/1991 | European Pat. Off. . |
| 0466413 | 1/1992 | European Pat. Off. ............. 128/903 |
| 1069619 | 5/1967 | United Kingdom . |
| 9110471 | 7/1991 | WIPO . |

Primary Examiner—William E. Kamm
Assistant Examiner—Marianne Parker
Attorney, Agent, or Firm—Richard L. Robinson

[57] ABSTRACT

A method and apparatus for processing data to be communicated between an implantable medical device and an external medical device to improve detectability of communication errors. An encoded block of data including message data and redundant data is processed by converting alternating data values of either the message data or the redundant data to respective complement data values. The altered block of data is communicated using relative pulse position modulation. The combination of alternating original and complement data with relative pulse position modulation (RPPM) takes advantage of the opposing adjacent errors characteristic of RPPM to decrease the probability of communication errors occurring in combinations that are undetectable by the decoding of the block of data.

34 Claims, 1 Drawing Sheet

METHOD AND APPARATUS FOR COMMUNICATING DATA BETWEEN MEDICAL DEVICES TO IMPROVE DETECTABILITY OF ERRORS

BACKGROUND OF THE INVENTION

1. Field of the Invention

The present invention generally relates to redundant data encoding schemes and data communication modulation schemes, and more particularly to a method and apparatus for communicating data between an implantable medical device and an external medical device that improves detectability of communication errors.

2. Background Information

There are many applications in which it is important to provide data communication that is substantially error-free. One such application is the programming of an implantable medical device such as a cardiac stimulator, which might be a pacemaker or a defibrillator, for example. Such devices are often programmed via an external medical device, known generally as a programmer, that includes a wand that can be located in proximity to the cardiac stimulator to establish a non-contacting communication link with the cardiac stimulator. The communication link can involve a transmitted electromagnetic signal that is modulated in accordance with the data to be communicated. The communication link requires an extremely high degree of reliability since any information going into the cardiac stimulator has the potential to immediately alter the therapeutic performance of that device.

When communicating information to or from an implantable medical device, it is a common practice to encode the information in a way that will increase the probability that errors in transmission will be detected. The encoding involves adding redundant information to the original message information to create coded information. In implantable medical devices, the most common type of encoding is a block code, where discrete packets of message information are encoded and the coded information is transmitted in discrete blocks.

When using a block code, the usual method for increasing the probability that errors will be detected is to increase the amount of redundant information. The disadvantages of this are a proportional increase in communication time and an increase in encoder/decoder hardware complexity to accommodate the larger block code size.

One known communication modulation technique is pulse-position-modulation (PPM). In PPM, pulses are transmitted and information is encoded as the time between a synchronization pulse and an information pulse. A derivative of PPM is relative-pulse-position-modulation (RPPM). In RPPM, information is encoded as the time interval between an information pulse and the immediately preceding information pulse.

In order to convey information in RPPM, the time position of each pulse must fall within a predefined window of time having a duration T that is located relative to the preceding pulse. The time window of duration T is divided into M time segments, each having a duration T/M. A pulse occurring in a particular one of the time segments is considered to represent a corresponding particular piece of information. In a binary RPPM system, M=2 and the two time positions represent the binary values 0 and 1. In a 4-bit nibble RPPM system, M=16 and the 16 time positions represent the 4-bit binary values 0000 through 1111, which can also be expressed as decimal values 0 through 15.

In RPPM communication systems, errors will manifest themselves as (a) additional pulses, (b) missing pulses, or (c) time-shifted pulses. Pulses occurring outside of the predefined time window T will be classified as range errors and will be detected by reception hardware prior to error detection decoding. The responsibility of the error detection decoding is then limited to detecting those errors, primarily pulses that are time-shifted within time window T, that are not detected by the reception hardware.

In RPPM communication systems, time-shifted pulses will cause opposing adjacent errors in the data. An error which shifts the time position of a pulse one time segment T/M too late will result in the preceding interval being decoded as a value one greater than correct, and the subsequent interval will be decoded as a value one less than correct. As an example, assume a block of four sequential nibbles with values of 13, 10, 3, and 7 is transmitted. The first two nibbles are defined by three sequential pulses. If the second pulse is time-shifted to cause the first nibble to appear as 14, the second nibble will appear as 9. The remaining nibbles would not be affected by the single pulse position error. In this example, a single pulse-position error results in opposing adjacent errors in the sequential data, in that the first data value appears greater than the correct value, and the second adjacent data value appears smaller than the correct value.

Prior art standard block code does not exploit the opposing adjacent errors characteristic of RPPM for error detection. For example, assume a standard block code where the redundant information is the complement of the message information, according to the following table.

| Original Data | | Complement Data | |
|---|---|---|---|
| Binary | Decimal | Binary | Decimal |
| 0000 | 0 | 1111 | 15 |
| 0001 | 1 | 1110 | 14 |
| 0010 | 2 | 1101 | 13 |
| 0011 | 3 | 1100 | 12 |
| 0100 | 4 | 1011 | 11 |
| 0101 | 5 | 1010 | 10 |
| 0110 | 6 | 1001 | 9 |
| 0111 | 7 | 1000 | 8 |
| 1000 | 8 | 0111 | 7 |
| 1001 | 9 | 0110 | 6 |
| 1010 | 10 | 0101 | 5 |
| 1011 | 11 | 0100 | 4 |
| 1100 | 12 | 0011 | 3 |
| 1101 | 13 | 0010 | 2 |
| 1110 | 14 | 0001 | 1 |
| 1111 | 15 | 0000 | 0 |

A single pulse-position error in the pulses conveying the message data will affect two message data nibbles due to the opposing adjacent errors characteristic of RPPM. A single pulse-position error in the corresponding pulses conveying the redundant data can affect two redundant data nibbles in a direction opposite to that of the first error so as to make the errors in the block undetectable. For example, a 4 nibble message may be 13, 10, 3, 7, and the resulting block code (message+complement) would be 13, 10, 3, 7, 2, 5, 12, 8.

A single pulse-position error in the second pulse such that the pulse is detected one T/M interval too late would create the code 14, 9, 3, 7, 2, 5, 12, 8 which would be detectable as an error since the first two message elements 14, 9 would fail a comparison with their complement redundant elements 2, 5. However, an additional error in the sixth pulse such that the pulse is detected one T/M interval too soon would create the code 14, 9, 3, 7, 1, 6, 12, 8 which would be an undetectable error. The first two message elements 14, 9 would pass a comparison with their complement redundant elements 1, 6. Thus, two pulse-position errors occurring in an eight element block could result in data errors that are undetectable. The likelihood of this error combination is the same as that for a similar pulse position modulated system which does not have the opposing adjacent errors characteristic.

SUMMARY OF THE INVENTION

The present invention involves processing of redundant encoded block code to take advantage of the phenomenon of opposing adjacent errors in relative pulse position modulation systems to improve detectability of communication errors. The result is increased error detection performance with no increase in the block code size.

In accordance with one aspect of the present invention, a method of processing data to be communicated between an implantable medical device and an external medical device to improve detectability of communication errors is presented including the following steps performed in at least one of the implantable and external medical devices. A first block of data is generated including a message data portion and a redundant data portion, with the message data portion including a plurality of message data values and the redundant data portion including at least one redundant data value having a predefined redundant relationship to at least one of the plurality of message data values. The first block of data is altered by converting alternating data values of at least one of the data portions of the first block of data to respective complement data values. A signal is generated including a sequence of relative pulse position modulated pulses, wherein each pulse is positioned at a time interval relative to the immediately preceding pulse that is representative of a corresponding one of the data values of the altered block of data.

In accordance with another aspect of the present invention, in a medical device, a communications circuit is provided for processing data to be communicated for improved detectability of communication errors. The communications circuit includes a block encoder adapted and configured to receive data to be processed and to encode a portion of the received data into a first block of data including a message data portion and a redundant data portion. The message data portion includes a plurality of message data values and the redundant data portion including at least one redundant data value having a predefined redundant relationship to at least one of the plurality of message data values. A data converter is provided that is adapted and configured to receive the first block of data from the block encoder and alter the first block of data by converting alternating data values of at least one of the data portions of the first block of data to respective complement data values. A signal generator is adapted and configured to receive the altered block of data and generate a signal including a sequence of relative pulse position modulated pulses, wherein each pulse is positioned at a time interval relative to the immediately preceding pulse that is representative of a corresponding one of the data values of the altered block of data.

In accordance with yet another aspect of the present invention, in a medical device, a communications circuit is provided for processing data that has been communicated for improved detectability of communication errors. The communications circuit includes a signal decoder adapted and configured to receive a signal including a sequence of relative pulse position modulated pulses, wherein each pulse is positioned at a time interval relative to the immediately preceding pulse, and to decode the signal to generate a block of data including a plurality of data values wherein each data value is representative of a corresponding one of the time intervals, the block of data including a message data portion having a plurality of message data values, and a redundant data portion having at least one redundant data value, wherein alternating data values of at least one of the data portions of the block of data are encoded as complement data values of original data values. A data converter is adapted and configured to receive the block of data from the signal decoder and alter the block of data by converting the encoded alternating data values to respective complement data values, thereby restoring putative original data values. An error detector is adapted and configured to receive the altered block of data from the data converter and compare data values of the message data portion to data values of the redundant data portion to determine whether the message and redundant data values are related according to a predetermined redundant relationship, thereby providing detection of communication error.

It is an object of the present invention to provide an improved method of communicating data between medical devices that provides for increased detectability of communication errors.

Other objects and advantages of the present invention will be apparent from the descriptions below and the drawings to which they refer.

DESCRIPTION OF THE PREFERRED EMBODIMENT

Figure 1:
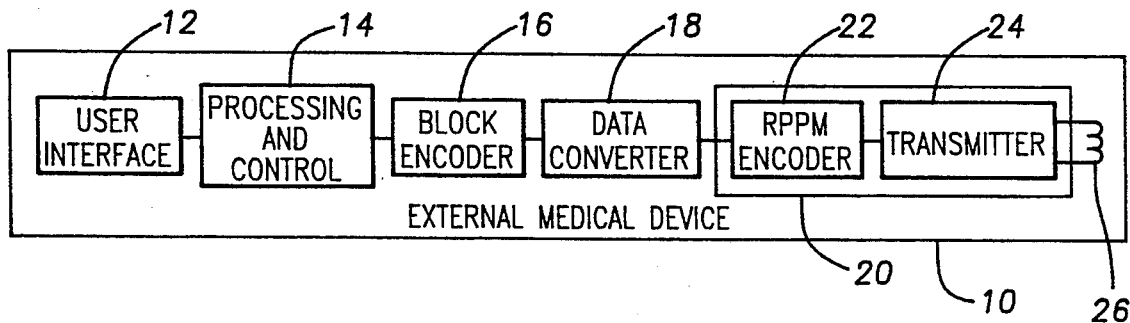
FIG. 1 is a block diagram of an external medical device configured in accordance with the present invention.

In accordance with the method of the present invention, the invention involves alternating the polarity (between normal and complement) of the redundant information in a coded block of data to be communicated by a train of relative pulse position modulated pulses, to exploit the opposing adjacent errors characteristic. By alternating the redundant information between normal and complement on an interval-by-interval basis, a single pulse-position error in the message information will not be rendered undetectable by a corresponding single pulse-position error in the redundant information. Recall that the opposing adjacent errors characteristic causes single errors to affect adjacent intervals in opposite directions. If the redundant information is inverted every other interval, a single error in the redundant information will cause adjacent errors to be in the same direction, thereby ensuring a detectable error. For example, using the same 4 nibble message as in the previous example, the resulting code (message+alternating normal/complement) would be:

13, 10, 3, 7, 13, 5, 3, 8.

A single error in the second pulse such that the pulse is detected one T/M interval too late would result in the code:

14, 9, 3, 7, 13, 5, 3, 8 which would be detectable as an error since the first two message elements 14, 9 would fail e comparison with their redundant elements 13, 5. An additional error in the sixth pulse such that the pulse is detected one T/M interval too soon would result in the code:

14, 9, 3, 7, 12, 6, 3, 8 which again would be detectable as an error since the first message element 14 would fail a comparison with its redundant element 12, even though the second message element 9 would not fail a comparison with its redundant complement element 6.

While this method does not completely eliminate the possibility of undetectable errors, it reduces their probability by extending the effects of errors onto neighboring message elements. Using the previous example, two additional errors, for a total of four errors in a block of eight elements, would be required for the errors to remain undetectable. An additional error in the fifth pulse such that the pulse is detected two T/M intervals too soon and in the ninth pulse such that the pulse is detected two T/M intervals too late would result in the code:

14, 9, 3, 5, 14, 6, 3, 10.

This combination of errors in one coded block would be undetectable.

The method of the invention has been illustrated above in the context of one type of redundant block encoding, but it should be appreciated that the principles of the invention can be applied to other redundant encoding schemes. An important principle of the invention is the inversion of adjacent data values prior to transmission of the data in a relative pulse position modulated signal. This inversion may be applied to any block code, but the choice of which portions of the block code to invert will depend upon the nature of the redundant encoding scheme, as described further below.

In contrast to the examples given above, there are block codes that do not have a one-to-one correspondence between message data values and redundant information data values. An example of such a block code is a parity code. In a parity code, the redundant information is the modulo-sum of the message data. For example, a parity block code a, b, c, d, e may have message values a, b, c, and d, and redundant information value e where $e = a \oplus b \oplus c \oplus d$ and $\oplus$ represents the modulo-sum operator. An example of such a parity block code using 4-bit nibble data values is:

15,2,8,9,2.

In an RPPM signal transmitting this parity block code, a single error in the second pulse such that the pulse is detected one T/M interval too soon would create the code 14,3,8,9,2.

The error would be undetectable because the modulo-sum of the message values is not changed.

By applying the principles of the invention to the parity block code, the single pulse-position error of the previous example would not go undetected. This is accomplished by alternating the polarity of adjacent message data values. For example, using the same four nibble message as in the previous example, the resulting code (alternating normal/complement message+ redundant) would be 15, 13, 8, 6, 2.

A single error in the second pulse such that the pulse is detected one T/M interval too soon would result in the code 14, 14, 8, 6, 2 which would result in the error being detectable where the receiver inverts the received data prior to applying the parity test. The receiver would interpret the block code to be 14, 1, 8, 9, 2. $14 \oplus 1 \oplus 8 \oplus 9 = 0$, which is not equal to 2.

The inversion of adjacent data values takes advantage of the opposing adjacent errors characteristic of RPPM to improve the error detection capabilities of any block code. When the inversion is applied is dependent upon the chosen block code.

Referring to FIG. 1, there is illustrated a block diagram of an external medical device 10 such as a programmer that can be used to communicate data to an implantable medical device. External medical device 10 includes a user interface 12 for human interaction that can include output devices such as a display screen or a printer, and input devices such as a keyboard or a light pen used in conjunction with a display screen. User interface 12 is connected to processing and control circuitry 14 that can include a microprocessor and associated circuits for generating data to be communicated to an implantable medical device. Data generated by processing and control circuitry 14 in response to user input via user interface 12 is processed by subsequent circuit blocks illustrated as block encoder 16, data inverter 18, and signal generator 20. The latter block is further illustrated as comprising a relative pulse position modulation encoder 22 and a transmitter 24 connected to an antenna coil 26. Data from processing and control circuitry 14 is received by block encoder 16 and is encoded in known fashion as a block of data comprising a message data portion and a redundant data portion. The message data portion includes a plurality of message data values and the redundant data portion includes at least one redundant data value having a predefined redundant relationship to at least one of the plurality of message data values. By way of example, the message data portion can include a block of four message data values representing information to be communicated and the redundant data portion can include another block of four redundant data values where each redundant data value corresponds to one of the message data values. Each redundant data value has a predefined relationship to its corresponding message data value and can be, for example, a duplicate of the message data value or, alternatively, the complement of the message data value. Other block encoding schemes can be employed where there is not a one-to-one correlation between the message data values and the redundant data values. For example, a parity code block code could be used in which a single redundant data value could represent the modulo-sum of a plurality of message data values.

Block coded data from block encoder 16 is received by data converter 18 which is configured to alter each block of data so received by converting alternating data values of at least one of the message or redundant data portions of the block to respective complement data values. Where there is a one-to-one correspondence between the message data values and the redundant data values in the coded block, the advantages of the present invention are realized when alternate data values of either the message data portion or the redundant data portion, but not both, are converted to respective complement data values. Where the block encoding scheme employed results in one of the message data portion or the redundant data portion of the block code having a greater number of data values than the other data portion, the advantages of the present invention are realized by converting to respective complement data values alternating data values of only the data portion having the greater number of data values.

Figure 2:
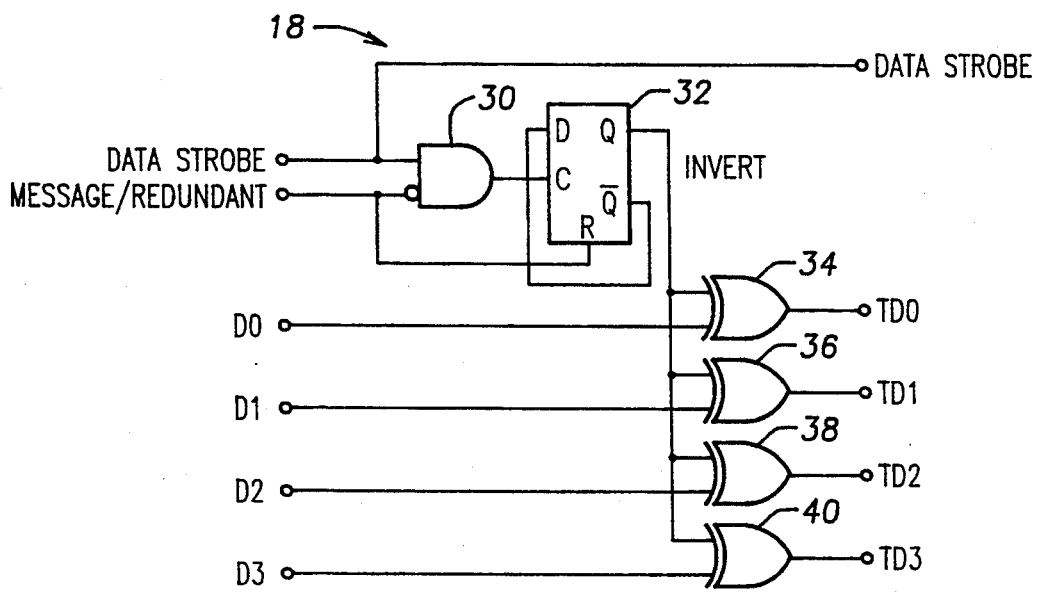
FIG. 2 is a schematic diagram of the data converter of the block diagram of FIG. 1, constructed in accordance with the present invention.

Referring in particular to FIG. 2, there is illustrated a schematic diagram of one embodiment of a data converter 18 in accordance with the present invention. Inputs from block encoder 16 include a DATA STROBE signal line, a MESSAGE/REDUNDANT signal line, and four input data lines D0, D1, D2 and D3. Outputs to RPPM encoder 22 include the DATA STROBE signal line and four output data lines TDO, TD1, TD2 and TD3. The illustrated embodiment is based upon a system in which data values are conveyed in 4-bit nibbles. This is intended to illustrate the concept only, and it should be understood that binary or 8-bit or other data schemes can be used, if desired. Data received on input lines D0–D3 is either passed through unchanged to output lines TD0–TD3, or all four bits of alternately received data nibbles are inverted so as to pass through the complement of the data nibble received, depending upon the state of the MESSAGE/REDUNDANT line. The DATA STROBE line is connected to one input of AND gate 30, and the MESSAGE/REDUNDANT line is connected to the other inverted input of AND gate 30. The MESSAGE/REDUNDANT line is also connected to the reset input R of D flip-flop 32. The output of AND gate 30 is connected to the clock input C of D flip-flop 32. The $\overline{Q}$ output of D flip-flop 32 is tied back to the D input of flip-flop 32. The Q output of flip-flop 32 is connected to the INVERT line which is connected to one input of each of EXCLUSIVE OR gates 34, 36, 38 and 40. Data lines D0–D3 are connected to the other input of each EXCLUSIVE OR gate 34–40, respectively. The outputs of EXCLUSIVE OR gates 34–40 are connected to output data lines TD0–TD3, respectively.

Data converter 18 of FIG. 2 operates as follows. A series of regularly spaced timing pulses are received on the DATA STROBE line. Each timing pulse is related to a new nibble of data on data input lines D0–D3. The MESSAGE/REDUNDANT line is either in a high or low state depending on whether the current data nibble is part of the message data portion or the redundant data portion of the block code being received. Assuming that message data is present at D0–D3, the MESSAGE/REDUNDANT line will be held high by preceding block encoder 16. The output of AND gate 30 therefore remains low regardless of the state of the DATA STROBE line and no clock signal is conveyed to flip-flop 32. The Q output of flip-flop 32 remains low and data passes through EXCLUSIVE OR gates 34–40 unchanged. Following the last message data nibble and prior to the first redundant data nibble, block encoder 16 causes MESSAGE/REDUNDANT line to go low, which releases the reset of flip-flop 32. A subsequent pulse on the DATA STROBE line will result in a rising edge clock signal from the output of AND gate 30 to latch the Q output of flip-flop 32 high, resulting in a high state being present on the INVERT line and at one input of each of EXCLUSIVE OR gates 34–40. The output of each EXCLUSIVE OR gate is therefore the inverse state of the input from the respective data input lines D0–D3. Consequently, the first data nibble on output data lines TD0–TD3 following the MESSAGE/REDUNDANT line going low is the complement of the data nibble present at data input lines D0–D3. The INVERT line remains high until the next rising edge of a pulse on the DATA STROBE line, at which time the rising edge clock signal from the output of AND gate 30 latches the Q output of flip-flop 32 low, in accordance with the state of the $\overline{Q}$ output from the previous cycle, where the $\overline{Q}$ output is tied back to the D input. The INVERT line consequently goes low, and EXCLUSIVE OR gates 34–40 cease their inverting function for the current data nibble. It should be appreciated that so long as the MESSAGE/REDUNDANT line remains low, meaning that redundant data is being processed, the flip-flop 32 and EXCLUSIVE OR gates 34–40 will cause alternate nibbles of data received on data input lines D0–D3 to be converted to their complements on data output lines TD0–TD3. While the embodiment illustrated in FIG. 2 has been configured to invert odd-numbered data nibbles of the redundant data portion of the block code received from block encoder 16, it should be appreciated that even-numbered data nibbles could be inverted instead, and the data nibbles of the message data portion could be inverted instead.

The altered block of data from data converter 18 is received by relative pulse position modulation (RPPM) encoder 22 and transmitter 24 of signal generator 20 in which a signal is generated in known fashion to include a sequence of relative pulse position modulated pulses, wherein each pulse is positioned at a time interval relative to the immediately preceding pulse that is representative of a corresponding one of the data values of the altered block of data. The signal so generated is transmitted as electromagnetic energy by transmitter 24 via antenna coil 26, to be received by an implantable medical device.

Figure 3:
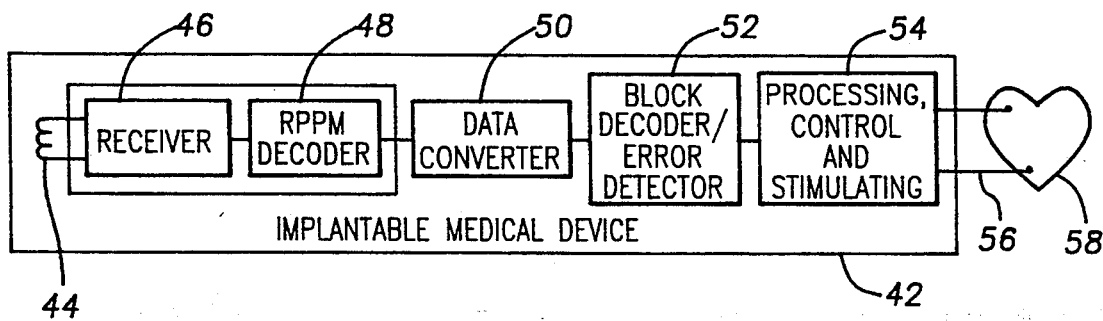
FIG. 3 is a block diagram of an implantable medical device configured in accordance with the present invention.

Referring to FIG. 3, there is illustrated a block diagram of an implantable medical device 42 such as a cardiac stimulator, which might be a pacemaker or cardioverter/defibrillator, capable of receiving data communicated from an external medical device such as the programmer of FIG. 1. Implantable medical device 42 includes an antenna coil 44 and associated receiver 46 for receiving data in the form of an encoded electromagnetic signal from the external medical device. Since the implantable medical device illustrated in FIG. 3 is particularly configured to take advantage of the data communications scheme of the present invention for enhanced detection of communication errors, it should be assumed for the purpose of understanding the functioning of the illustrated embodiment that the signal to be received and processed has been previously processed prior to transmission according to the principles of the invention described above with respect to the external medical device of FIGS. 1 and 2.

The signal received in receiver 46 is in the form of an altered block code having a message data portion including a plurality of message data values and a redundant data portion including at least one redundant data value, wherein alternating data values of at least one of the data portions are encoded as complement data values of original data values. The altered block code is received and passed on to relative pulse position modulation (RPPM) signal decoder 48 in the form of a sequence of RPPM pulses, wherein each pulse is positioned at a time interval relative to the immediately preceding pulse. RPPM decoder 48 decodes the signal in known fashion to generate a block of data including a plurality of data values wherein each data value is representative of a corresponding one of the time intervals.

The block of data from RPPM signal decoder 48 is received by data converter 50 which is configured similarly to data converter 18 of FIGS. 1 and 2 to alter the decoded block of data by converting the encoded alternating data values to respective complement data values, thereby restoring the putative original data values of the original block code as they existed prior to processing for transmission. It should be understood that data converter 50 is configured to accommodate the particular block code and code altering scheme that was employed during processing of the original data for transmission. For example, if the odd-numbered data values of the redundant data portion of the block code were inverted to their respective complement data values in the external medical device prior to transmission, then the odd-numbered data values of the redundant data portion of the block code received from RPPM signal decoder 48 are likewise inverted again. Barring communication errors, the block code from data converter 50 should be identical to the block code generated by block encoder 16 of the external medical device.

Block decoder/error detector 52 receives the altered (putatively restored) block of data from data converter 50 and compares the data values of the message data portion of the block of data to the data values of the redundant data portion of the block of data to determine whether the message data values and redundant data values are related according to their predetermined redundant relationship. If they are so related, the redundant data is stripped off and the message data is passed on to processing, control and stimulating circuitry 54 for further processing in known fashion. If they are not so related, then an error has occurred during communication and the block of data must be rejected as being unreliable. In that event, an error signal is sent to processing, control and stimulating circuitry 54 for further processing in known fashion. Processing, control and stimulating circuitry 54 includes circuitry for transmitting a cardiac stimulating signal via one or more implantable leads 56 to heart 58.

While the present invention has been illustrated and described with particularity in terms of a preferred method and preferred embodiments, it should be understood that no limitation of the scope of the invention is intended thereby. The scope of the invention is defined only by the claims appended hereto. It should also be understood that variations of the particular embodiments described herein incorporating the principles of the present invention will occur to those of ordinary skill in the art and yet be within the scope of the appended claims. For example, the data processing scheme of the present invention has been described in the context of alternating data inversion occurring prior to transmission in an external medical device, and alternating data inversion occurring subsequent to reception in an implantable medical device. It will be obvious to the ordinarily skilled artisan that the alternating data encoding could take place in the implantable device for transmission to an external device for decoding.

I claim:

1. A method of processing data to be communicated between an implantable medical device and an external medical device to improve detectability of communication errors, comprising the steps of:

in at least one of said implantable and external medical devices:
 a) generating a first block of data including a message data portion and a redundant data portion, said message data portion including a plurality of message data values and said redundant data portion including at least one redundant data value having a predefined redundant relationship to at least one of said plurality of message data values;
 b) altering said first block of data by converting alternating data values of at least one of said data portions of said first block of data to respective complement data values; and
 c) generating a signal including a sequence of relative pulse position modulated pulses, wherein each pulse is positioned at a time interval relative to an immediately preceding pulse that is representative of a corresponding one of the data values of said altered block of data.

2. The method of claim 1, wherein in said altering step said at least one of said data portions of said first block of data is said message data portion.

3. The method of claim 1, wherein in said altering step said at least one of said data portions of said first block of data is said redundant data portion.

4. The method of claim 1, wherein in said generating step there is a one-to-one correlation between each data value of said message data portion and each data value of said redundant data portion.

5. The method of claim 4, wherein in said altering step said at least one of said data portions of said first block of data is said message data portion.

6. The method of claim 4, wherein in said altering step said at least one of said data portions of said first block of data is said redundant data portion.

7. The method of claim 1, wherein in said generating step said message data portion includes a greater number of data values than said redundant data portion, and wherein in said altering step said at least one of said data portions of said first block of data is said message data portion.

8. The method of claim 1, wherein in said generating step said redundant data portion includes a greater number of data values than said message data portion, and wherein in said altering step said at least one of said data portions of said first block of data is said redundant data portion.

9. The method of claim 1, and further including the step of:
transmitting said generated signal externally of said at least one of said implantable and external medical devices.

10. The method of claim 9, and further including the step of:
receiving said transmitted signal in another medical device separate from the medical device from which the signal was transmitted.

11. The method of claim 10, and further including the step of:
decoding said received signal to generate a second block of data putatively corresponding to said altered block of data by interpreting each time interval between successively received pulses as representing a particular predefined data value.

12. The method of claim 11, and further including the step of:
converting said second block of data to a third block of data putatively corresponding to said first block of data by altering said second block of data by converting like alternating data values of a like data portion of said second block of data to respective complement data values.

13. The method of claim 12, and further including the step of:
comparing said data values of said redundant data portion of said third block of data to said data values of said message data portion of said third block of data to determine whether said predetermined redundant relationship is valid, thereby providing detection of error in said third block of data.

14. In a medical device, a communications circuit for processing data to be communicated for improved detectability of communication errors comprising:
block encoder means for receiving data to be processed and encoding a portion of said received data into a first block of data including a message data portion and a redundant data portion, said message data portion including a plurality of message data values and said redundant data portion including at least one redundant data value having a predefined redundant relationship to at least one of said plurality of message data values;
data converter means in circuit communication with said block encoder means for receiving said first block of data from said block encoder means and altering said first block of data by converting alternating data values of at least one of said data portions of said first block of data to respective complement data values; and
signal generator means in circuit communication with said data converter means for receiving said altered block of data and generating a signal including a sequence of relative pulse position modulated pulses, wherein each pulse is positioned at a time interval relative to an immediately preceding pulse that is representative of a corresponding one of the data values of said altered block of data.

15. The medical device of claim 14, wherein said at least one of said data portions of said first block of data is said message data portion.

16. The medical device of claim 14, wherein said at least one of said data portions of said first block of data is said redundant data portion.

17. The medical device of claim 14, wherein there is a one-to-one correlation between each data value of said message data portion and each data value of said redundant data portion.

18. The medical device of claim 17, wherein said at least one of said data portions of said first block of data is said message data portion.

19. The medical device of claim 17, wherein said at least one of said data portions of said first block of data is said redundant data portion.

20. The medical device of claim 14, wherein said message data portion, includes a greater number of data values than said redundant data portion, and wherein said at least one of said data portions of said first block of data is said message data portion.

21. The medical device of claim 14, wherein said redundant data portion includes a greater number of data values than said message data portion, and wherein said at least one of said data portions of said first block of data is said redundant data portion.

22. The medical device of claim 14, and further including transmitter means in circuit communication with said signal generator means for transmitting said generated signal externally of said medical device.

23. In a medical device, a communications circuit for processing data that has been communicated for improved detectability of communication errors comprising:
signal decoder means for receiving a signal including a sequence of relative pulse position modulated pulses, wherein each pulse is positioned at a time interval relative to an immediately preceding pulse, and decoding said signal to generate a block of data including a plurality of data values wherein each data value is representative of a corresponding one of the time intervals, said block of data including a message data portion having a plurality of message data values, and a redundant data portion having at least one redundant data value, wherein alternating data values of at least one of said data portions of said block of data are encoded as complement data values of original data values;
data converter means in circuit communication with said signal decoder means for receiving said block of data from said signal decoder means and altering said block of data by converting said encoded alternating data values to respective complement data values, thereby restoring putative original data values; and
error detector means in circuit communication with said data converter means for receiving said altered block of data from said data converter means and comparing data values of said message data portion to data values of said redundant data portion to determine whether said message and redundant data values are related according to a predetermined redundant relationship, thereby providing detection of communication error.

24. The medical device of claim 23, wherein said at least one said data portion of said block of data is said message data portion.

25. The medical device of claim 23, wherein said at least one of said data portions of said block of data is said redundant data portion.

26. The medical device of claim 23, wherein there is a one-to-one correlation between each data value of said message data portion and each data value of said redundant data portion.

27. The medical device of claim 26, wherein said at least one of said data portions of said block of data is said message data portion.

28. The medical device of claim 26, wherein said at least one of said data portions of said block of data is said redundant data portion.

29. The medical device of claim 23, wherein said message data portion includes a greater number of data values than said redundant portion, and wherein said at least one of said data portions of said block of data is said message data portion.

30. The medical device of claim 23, wherein said redundant data portion includes a greater number of data values than said message data portion, and wherein said at least one of said data portions of said block of data is said redundant data portion.

31. A system of medical devices comprising a first medical device and a second medical device separate from the first medical device,
said first medical device having a communications circuit for processing data to be communicated for improved detectability of communication errors including:
block encoder means for receiving data to be processed and encoding a portion of said received data into a first block of data including a message data portion and a redundant data portion, said message data portion including a plurality of message data values and said redundant data portion including at least one redundant data value having a predefined redundant relationship to at least one of said plurality of message data values;
data converter means in circuit communication with said block encoder means for receiving said first block of data from said block encoder means and altering said first block of data by converting alternating data values of at least one of said data portions of said first block of data to respective complement data values;
signal generator means in circuit communication with said data converter means for receiving said altered block of data and generating a signal including a sequence of relative pulse position modulated pulses, wherein each pulse is positioned at a time interval relative to an immediately preceding pulse that is representative of a corresponding one of the data values of said altered block of data; and
transmitter means in circuit communication with said signal generator means for transmitting said generated signal externally of said first medical device; and said second medical device including receiving means for receiving said transmitted signal.

32. The system of medical devices of claim 31, in which said second medical device further includes:
decoder means in circuit communication with said receiving means for decoding said received signal to generate a second block of data putatively corresponding to said altered block of data by interpreting each time interval between successively received pulses as representing a particular predefined data value.

33. The system of medical devices of claim 32, in which said second medical device further includes:
data converter means in circuit communication with said decoder means for converting said second block of data to a third block of data putatively corresponding to said first block of data by altering said second block of data by converting like alternating data values of a like data portion of said second block of data to respective complement data values.

34. The system of medical devices of claim 33, in which said second medical device further includes:
error detector means in circuit communication with said data converter means for comparing said data values of said redundant data portion of said third block of data to said data values of said message data portion of said third block of data to determine whether said predetermined redundant relationship is valid, thereby providing detection of communication error.

* * * * *